(12) United States Patent
Barmpounis et al.

(10) Patent No.: US 10,578,581 B2
(45) Date of Patent: Mar. 3, 2020

(54) PARTICLE MOBILITY ANALYZER

(71) Applicant: Technische Universiteit Delft, Delft (NL)

(72) Inventors: Konstantinos Barmpounis, Delft (NL); George Biskos, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 0 days.

(21) Appl. No.: 15/843,587

(22) Filed: Dec. 15, 2017

(65) Prior Publication Data
US 2018/0106760 A1   Apr. 19, 2018

Related U.S. Application Data

(63) Continuation of application No. PCT/NL2016/050416, filed on Jun. 10, 2016.

(30) Foreign Application Priority Data

Jun. 15, 2015 (NL) .................................. 2014969

(51) Int. Cl.
*G01N 27/62* (2006.01)
*G01N 15/02* (2006.01)
*H01J 49/00* (2006.01)
*G01N 15/00* (2006.01)

(52) U.S. Cl.
CPC ....... *G01N 27/622* (2013.01); *G01N 15/0266* (2013.01); *H01J 49/0013* (2013.01); *G01N 2015/0038* (2013.01); *G01N 2015/0046* (2013.01)

(58) Field of Classification Search
None
See application file for complete search history.

(56) References Cited

U.S. PATENT DOCUMENTS 4,769,609 A * 9/1988 Masuda ............. G01N 15/0266
324/455
5,973,904 A * 10/1999 Pui ........................ B05B 5/0533
361/225

(Continued)

FOREIGN PATENT DOCUMENTS

DE       10347656 A1 *  5/2005  ........... G01N 27/622
WO    2016/204609         12/2016

OTHER PUBLICATIONS

Intra et al., "An overview of differential mobility analyzers for size classification of nanometer-sized aerosol particles" (Year: 2007).*

(Continued)

*Primary Examiner* — Michael J Logie
(74) *Attorney, Agent, or Firm* — Peacock Law P.C.; Janeen Vilven; Justin Muehlmeyer

(57) ABSTRACT

Mobility analyzer comprising a first electrode and a second electrode, one of said electrodes being grounded and the other of said electrodes being connectable to a high-voltage source, which analyzer further comprises an aerosol inlet and a sheath flow outlet as well as at least one sample flow channel with a sample inlet and a sample outlet, wherein the electrodes are embodied in a plastic material provided with an electrically conductive coating.

8 Claims, 1 Drawing Sheet

(56) References Cited

U.S. PATENT DOCUMENTS

| | | | | |
|---|---|---|---|---|
| 5,992,244 | A * | 11/1999 | Pui | B01J 19/081 73/865.5 |
| 7,155,812 | B1 * | 1/2007 | Peterson | H01C 3/06 250/286 |
| 8,173,959 | B1 * | 5/2012 | Boumsellek | G01N 27/622 250/281 |
| 8,739,602 | B2 * | 6/2014 | Vize | G01N 15/0266 73/28.02 |
| 9,324,550 | B1 * | 4/2016 | Jones | G01N 27/622 |
| 2004/0080321 | A1 * | 4/2004 | Reavell | G01N 15/0266 324/458 |
| 2004/0232326 | A1 * | 11/2004 | Guevremont | G01N 27/624 250/287 |
| 2005/0083633 | A1 * | 4/2005 | Riebel | H01T 23/00 361/227 |
| 2006/0093737 | A1 * | 5/2006 | Dick | H01L 21/67028 427/180 |
| 2012/0099105 | A1 | 4/2012 | Vize et al. | |
| 2014/0262971 | A1 * | 9/2014 | Drumheller | G01N 27/622 209/127.1 |
| 2017/0103879 | A1 * | 4/2017 | Cooks | H01J 49/061 |

OTHER PUBLICATIONS

Kulkarni et al., "New Fast integrated mobility spectrometer for real-time measurement of aerosol sized distribution: II. Design calibration, and performance characterization", Journal of Aerosol science (Year: 2006).*

Anthanasopolous, "Electrical conductivity of polyurethane/ MWCNT nanocomposite foams", Polymer Composites, vol. 33, No. 8, 2012, 1302-1312.

Li, et al., "A miniature disk electrostatic aerosol classifier (mini-disk EAC) for personal nanoparticle sizers", Journal of Aerosol Science 40 (11), 2009, 982-992.

Mei, et al., "A cost-effective differential mobility analyzer (cDMA) for multiple DMA column applications", Journal of Aerosol Science 42 (7), 2011, 462-473.

* cited by examiner

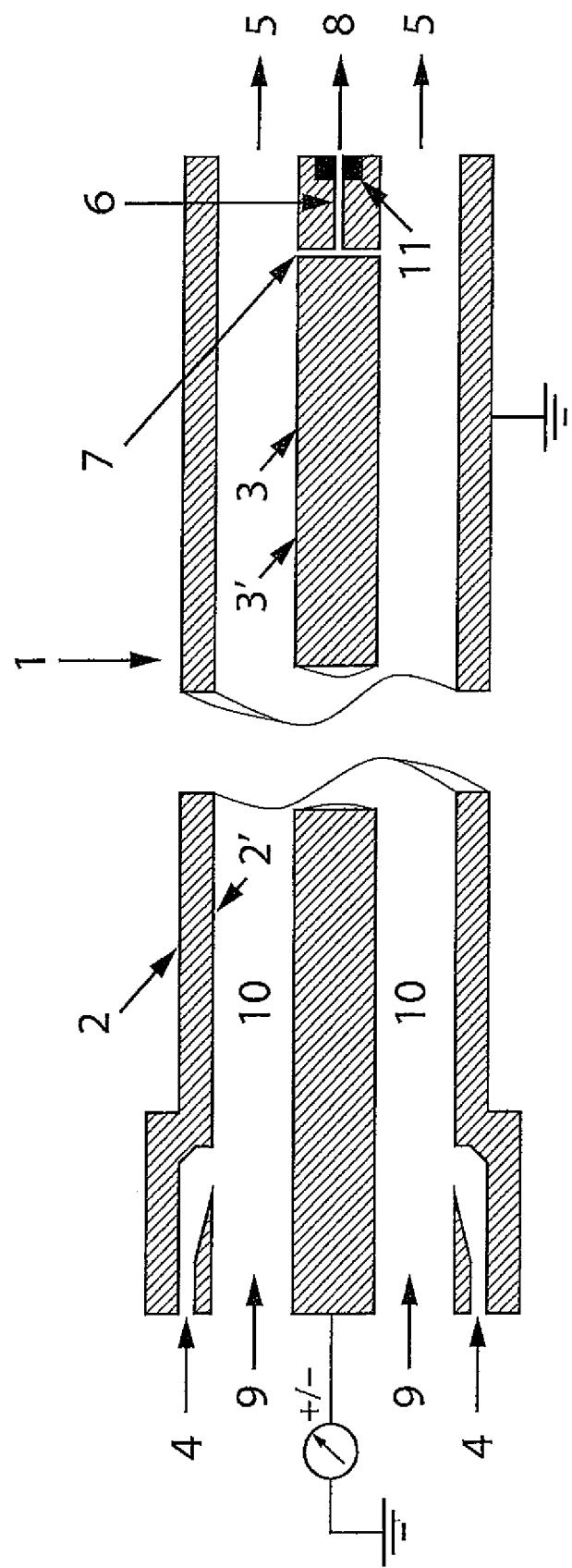

PARTICLE MOBILITY ANALYZER

CROSS-REFERENCE TO RELATED APPLICATIONS

This application is a continuation application of Patent Cooperation Treaty Application No. PCT/NL2016/050416, filed on Jun. 10, 2016, which claims priority to Netherlands Patent Application No. 2014969, filed on Jun. 15, 2015, and the specifications and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Field of the Invention (Technical Field)

The present invention relates to a particle mobility analyzer comprising a first electrode and a second electrode, one of said electrodes being grounded and the other of said electrodes being connectable to a voltage source, which analyzer further comprises an aerosol inlet and a sheath flow inlet and a sheath flow outlet, as well as at least one particle sample flow channel with a particle sample inlet and a particle sample outlet.

Description of Related Art Including Information Disclosed Under 37 C.F.R. §§ 1.97 and 1.98

Such a particle mobility analyzer is for instance disclosed by the review article, "An overview of differential mobility analyzers for size classification of nanometer-sized aerosol particles", by Panich Intra and Nakorn Tippayawong, published in the Songklanakarin Journal of Science and Technology 30(2), 243-256, March-April 2008. According to this article a differential mobility analyzer (DMA) is one of the most commonly used devices for classifying and measuring nanometer sized aerosol particles between 1 nm to 1 µm in diameter, which is based on their electrical mobility. In this article, several designs of known DMA's are disclosed.

A typical DMA essentially comprises two concentric metal electrodes with the inner electrode maintained at a controlled negative or positive voltage, typically ranging from 1 V to 10 kV, while the outer electrode is electrically grounded. This creates an electric field in an annular space between the two electrodes. A laminar stream of charged aerosol and a laminar stream of particle-free sheath air are introduced at one end of the DMA and flow down the annular space between the electrodes. The aerosol surrounds the inner core of sheath air, and both flows pass down the annulus with no mixing of the two laminar streams.

The electrical field between the electrodes causes charged particles to be attracted through the sheath air to the charged collector electrode. The location where the collected particles arrive at the collector electrode depends on the particle electrical mobility, the aerosol flow rate, and the DMA geometry. The electrical mobility of the collected particles is a function of the dimensions of the DMA, the applied voltage, and the aerosol flow rate.

Particles with a high electrical mobility are collected in the upstream region of the collecting electrode. Particles with a low electrical mobility are collected in the downstream region of the collecting electrode. Particles within a narrow range of electrical mobility exit the annular space between the electrodes through a small slit (the particle sample inlet) located in the downstream region of the collecting electrode. These particles are transferred through a particle sample flow channel to a particle sample exit so as to arrive at a further downstream positioned particle counter to determine the particle number concentration. The remaining particles are exhausted out as excess air flow. The particle size distribution can be determined by varying the differential voltage between the two electrodes of the DMA.

Said review article discusses several differential mobility analyzers which are all of the so-called tube type, wherein each design comprises a central rod or electrode usually of stainless steel with several centimeters thickness, and an outer chassis made of steel or aluminium, and also having a thickness of several centimeters.

From the article "Radial Differential Mobility Analyzer", by Shou-Hua Zhang et al, published in Aerosol Science and Technology 23: 357-372 (1995) a so-called radial design of a differential mobility analyzer is known which is said to be particularly suitable to measure ultrafine aerosol particles.

In this radial design embodied with two disks forming the electrodes of the design, particle free sheath air flow enters tangentially into a circular channel between the disks, and then passes through a ring made of porous material (for instance polyethylene) that evenly distributes the sheath flow and provides a uniform flow field. The aerosol flow is also introduced tangentially into an inlet channel of the radial DMA.

The airflow exits through an outlet that is positioned at the center of the housing disk, and the classified aerosol is extracted through a particle flow inlet in the electrode that is opposite to the aerosol inlet. The radial DMA disclosed in this article is made of stainless steel, aluminium, and plastic. Both electrodes, that is the housing disk electrode and an inlaid disk electrode are made of stainless steel.

In use, the housing is grounded. The electrical field in the analyzing region attracts charged particles from the aerosol layer and causes them to migrate across the sheath air flow toward the collecting electrode (that is the inlaid electrode) as the radial flow carries them towards the center of the instrument. Particles with relatively high mobility deposit on the electrode upstream of the particle sample inlet. Those with relatively low mobility are discharged with the excess aerosol flow. Particles within a narrow range of intermediate mobilities can reach the particle sample inlet and are extracted.

The article further mentions that other differential mobility analyzer geometries have also been reported, notably parallel plate analyzers. It also refers to a cumulative mobility analyzer as opposed to a differential mobility analyzer, that is based upon the flow between parallel circular disks.

This invention therefore relates to all such known differential or cumulative mobility analyzers, of all known types such as according to the types of the tube design, the radial design, and any other known design.

Although the known designs exist at great variety, there remain of course inherent limitations in how the mobility analyzers can be manufactured or built. These limitations are in part due to the materials that are required to be used for the mobility analyzers, which are solid metals. These metals are required because of their necessary electrically conductive properties.

BRIEF SUMMARY OF THE INVENTION

It is an object of the invention to provide a mobility analyzer of a construction which is not limited to the known shapes and designs, and which brings about advantages particularly in terms of versatility and portability.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 1 depicts a differential mobility analyzer according to the invention shown in a cross-sectional side view.

DETAILED DESCRIPTION OF THE INVENTION

According to the invention a mobility analyzer is proposed having the features of one or more of the appended claims.

In a first aspect of the invention the electrodes of the mobility analyzer are embodied in a plastic material provided with either a conductive material embedded in the plastic material, or an electrically conductive coating provided on the plastic material. It is also possible to apply both measures simultaneously, that is to apply a conductive material embedded in the plastic material, and an electrically conductive coating provided on the plastic material.

Wherein the conductive material is embedded in the plastic material it is preferred that the conductive material is embodied in carbon nanotubes. The article "Electrical conductivity of polyurethane/MWCNT Nanocomposite Foams", by N. Athanasopoulos et al, Polymer Composites—2012, published online in wileyonlinelibrary.com, Society of Plastics Engineers discloses a manufacturing method therefore.

Manufacturing a mobility analyzer with a core of essentially plastic rather than steel or aluminium is highly advantageous since many simple and inexpensive manufacturing techniques, such as 3-D printing, can be used providing the possibility to reduce the manufacturing costs and to bring more variety in the shape and design of the mobility analyzer. Furthermore the invention opens up the possibility to choose from a vast number of materials having a significantly lower density than the usually applied metals, thereby reducing the total weight of the mobility analyzer which makes it portable and improves its versatility of use.

Suitably the electrically conductive coating provided on the plastic core is a metallic coating.

Preferably further the electrode being grounded embodies the analyzer's housing.

Particularly when the mobility analyzer is of the type wherein the electrodes are concentrically arranged with respect to each other, thus defining an annular channel for the aerosol in between said electrodes, and wherein an inner electrode of said electrodes is provided with said sample inlet that provides access to the sample flow channel for guiding particles captured from the aerosol to a particle counter, one of the further advantages that the invention provides is that the particle counter can be arranged in the sample flow channel within the inner electrode. This proximate placement of the particle counter improves the accuracy of the instrument tremendously.

The invention will hereinafter be further elucidated with reference to the drawing of a single FIGURE of an exemplary embodiment of a mobility analyzer of the invention, and with reference to a manufacturing method resulting in a differential mobility analyzer according to the invention that is not limiting as to the appended claims.

In an example to demonstrate a method of manufacturing a differential mobility analyzer according to the invention, such an analyzer is manufactured based on an existing custom-made cylindrical stainless steel DMA having five metallic parts; i.e., the inner and outer electrode, the aerosol entrance slit, and an inlet and outlet base.

Flexible silicone rubber was used to create a mold for each part of the DMA. To do so, each piece was placed inside a container and liquid silicone rubber was poured until the concerning piece was fully submerged. The metallic pieces were removed from their molds after approximately 1 hour that was required for the silicone to harden. Liquid polyurethane was then poured in the mold and was allowed to solidify. In order to make the inner surface of the plastic DMA conductive, all its parts were spray-coated with Nickel paint.

Three cycles of the mentioned spraying/drying process were sufficient to achieve full coverage of the surface, yielding a 0.5-mm thick conductive film on the surface of each part. The weight of the resulting plastic DMA after its assembly is 150 g, which is significantly lighter than that of the corresponding stainless steel DMA (3.5 kg), while the cost of the materials used for manufacturing the DMA of the invention are in the order of ca. 100 US dollars. Considering that multiple DMAs can be produced from a single mold, the manufacturing time and associated cost can be further reduced, making the proposed method extremely attractive.

Instead of using molds for making the polyurethane parts of the mobility analyzer, it is also possible to provide the said plastic parts by 3-D printing which brings about even more versatility in the shapes and designs that can be realized.

As an alternative to the just mentioned two methods of manufacturing a mobility analyzer according to the invention, it is also possible to apply the manufacturing steps of:
  providing a mold or molds for the parts of the mobility analyzer;
  pouring a liquid plastic material in the mold or molds;
  embedding a conductive material, preferably carbon nanotubes, in the liquid plastic material;
  allowing the plastic material with the embedded conductive material to solidify in the mold or molds to provide said parts of the mobility analyzer;
  removing the parts from the mold or molds;
  optionally providing a conductive coating on the parts;
  and finally assembling the parts together to provide the mobility analyzer. The skilled person knows how to embed the conductive material in the liquid plastic material by adopting the teaching of the above-mentioned article "Electrical conductivity of polyurethane/MWCNT Nanocomposite Foams", by N. Athanasopoulos et al, Polymer Composites—2012, published online in wileyonlinelibrary.com, Society of Plastics Engineers.

FIG. 1 depicts a differential mobility analyzer according to the invention shown in a cross-sectional side view.

The analyzer bears reference 1 and comprises a first electrode 2 and a second electrode 3, one 2 of said electrodes being grounded and the other 3 of said electrodes being connectable to a high-voltage source which can be either a positive voltage or a negative voltage. The analyzer 1 further comprises an aerosol inlet 4 and a sheath flow inlet 9 and sheath flow outlet 5 as well as at least one particle sample flow channel 6 with a particle sample inlet 7 and a particle sample outlet 8. Further there is an inlet 9 for sheath gas.

According to the invention the electrodes 2, 3 are embodied in a plastic material provided either with conductive material embedded therein, or provided with an electrically conductive coating 2', 3' on the plastic material. Wherein the conductive material is embedded in the plastic material, it is preferable to use therefore carbon nanotubes. In addition, or alternative, to embedding a conductive material in the plastic material, it is according to the invention possible to apply a conductive coating on the plastic material. Preferably the electrically conductive coating 2', 3' is a metallic coating. The FIGURE shows further that the electrode 2 being grounded embodies the analyzer's housing.

The shown mobility analyzer 1 has electrodes 2, 3 that are concentrically arranged with respect to each other, thus defining an annular channel 10 for the aerosol in between said electrodes 2, 3.

When the DMA of the invention is used the inner electrode 3 is maintained at a controlled negative or positive voltage, ranging from 1 V to for instance 10 kV or higher, while the outer electrode 2, which embodies the housing, is electrically grounded. This creates an electric field between the two electrodes 2, 3. A laminar stream of charged aerosol introduced at inlet 4 and a laminar stream of particle-free sheath air introduced at inlet 9 flow down in the annular channel 10 between the electrodes 2, 3. The aerosol therewith surrounds an inner core of sheath air, and both flows pass down channel 10 with no mixing of the two laminar streams.

The electrical field between the electrodes 2, 3 causes charged particles to be attracted through the sheath air to the charged collector electrode 3. The location where the collected particles arrive at the collector electrode 3 depends on the particle electrical mobility, the aerosol flow rate, and the DMA geometry. The electrical mobility of the collected particles is a function of the dimensions of the DMA, the applied voltage, and the aerosol flow rate.

Particles with a high electrical mobility are collected in the upstream region A of the collecting electrode 3. Particles with a low electrical mobility are collected in the downstream region B of the collecting electrode 3. Particles within a narrow range of electrical mobility exit the annular channel 10 between the electrodes 2, 3 through the particle sample inlet 7 located in the downstream region B of the collecting electrode 3. These particles are transferred through a particle sample flow channel 6 to a particle sample exit 8.

Normally after leaving the sample exit 8, the particles arrive at a further downstream and externally of the DMA positioned particle counter to determine the particle number concentration. In the FIGURE, an embodiment is shown that is enabled by the invention and in which the particle counter 11 is arranged in the sample flow channel 6 within the inner electrode 3. This increases the reliability and accuracy of the DMA of the invention when used for determining particle number concentrations.

Although the invention has been discussed in the foregoing with reference to an exemplary embodiment of the apparatus of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

What is claimed is:

1. A mobility analyzer comprising a first electrode film and a second electrode film, one of the electrode films being grounded and another of the electrode films being connectable to a voltage source, which mobility analyzer further comprises an aerosol inlet and a sheath flow-inlet and a sheath flow-outlet as well as at least one particle sample flow channel with a particle sample inlet and a particle sample outlet, wherein each of the electrode films coat a plastic material, and wherein the electrodes are concentrically arranged with respect to each other thus defining an annular channel for an aerosol in between said electrodes, and wherein an inner electrode of the electrodes is provided with the particle sample inlet that provides access to the particle sample flow channel for guiding particles captured from the aerosol to a particle counter, and the particle counter is arranged in the particle sample flow channel within the inner electrode.

2. The mobility analyzer according to claim 1, wherein the conductive material is embodied in carbon nanotubes.

3. The mobility analyzer according to claim 1, wherein the electrically conductive coating is a metallic coating.

4. The mobility analyzer according to claim 1, wherein the electrode being grounded embodies the mobility analyzer's housing.

5. A method for manufacturing a mobility analyzer according to claim 1, comprising the steps of:
  providing a mold or molds for the parts of the mobility analyzer;

pouring a liquid plastic material in the mold or molds;

embedding the conductive material in the liquid plastic material;

allowing the plastic material with the embedded conductive material to solidify in the mold or molds to provide said parts of the mobility analyzer;

removing the parts from the mold or molds;

optionally providing the electrically conductive coating on the parts; and assembling the parts together to provide the mobility analyzer.

6. The method of claim 5 wherein embedding the conductive material comprises embedding carbon nanotubes.

7. A method for manufacturing a mobility analyzer according to claim 1, comprising the steps of:

providing a mold or molds for the parts of the mobility analyzer;

pouring a liquid plastic material in the mold or molds and allowing the plastic material to solidify in the mold or molds to provide plastic material parts;

removing the plastic material parts from the mold or molds;

spraying an electrically conductive coating on the plastic material parts; and assembling the plastic material parts together to provide the mobility analyzer.

8. A method for manufacturing a mobility analyzer according to claim 1, comprising the steps of:

providing plastic material parts by 3-D printing;

spraying an electrically conductive coating on the plastic material parts; and assembling the plastic material parts together to provide the mobility analyzer.

* * * * *